US006221913B1

(12) United States Patent
Petrie et al.

(10) Patent No.: US 6,221,913 B1
(45) Date of Patent: Apr. 24, 2001

(54) DIALKYL UREAS AS CALCITONIN MIMETICS

(75) Inventors: Charles R. Petrie; Patricia A. McKernan, both of Woodinville; Emma E. Moore, Seattle, all of WA (US); John M. Ostresh, Encinitas, CA (US); Jean-Philippe Meyer, Holland, PA (US); Richard A. Houghten, Del Mar; Clemencia Pinilla, Cardiff, both of CA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/233,893

(22) Filed: Jan. 20, 1999

Related U.S. Application Data
(60) Provisional application No. 60/072,987, filed on Jan. 21, 1998.

(51) Int. Cl.[7] .................. A61K 31/17; A61K 31/195; A61K 31/24; A61K 31/40
(52) U.S. Cl. .................. 514/596; 514/419; 514/542; 514/564; 514/586; 514/878; 548/496; 560/34; 562/439; 564/27; 564/48
(58) Field of Search ................ 514/419, 542, 514/564, 586, 596, 878; 548/496; 560/34; 562/439; 564/27, 48

(56) References Cited

U.S. PATENT DOCUMENTS 4,840,967 * 6/1989 Beeley et al. .................. 514/466

FOREIGN PATENT DOCUMENTS 355819     2/1990  (EP) .

OTHER PUBLICATIONS

Wener et al., *Endocrinology* 90: 752–759, 1972.
McLeod et al., *Endocrine Res. Communications* 8(1): 49–59, 1981.
Tashjian et al., Recent Progress in Hormone Res. 34: 285–334, 1978.
Raisz et al, *Am. J. Medicine:* 43: 684–690, 1967.

* cited by examiner

*Primary Examiner*—Peter O'Sullivan
(74) *Attorney, Agent, or Firm*—Susan E. Lingenfelter

(57) ABSTRACT

Dialkyl urea compounds are described which act as calcitonin mimetics. These compounds are useful in the treatment of diseases which are associated with bone resorption. The calcitonin mimetics of the present invention are also useful in assays for the determination of calcitonin receptor activity.

13 Claims, No Drawings

DIALKYL UREAS AS CALCITONIN MIMETICS

This application claims benefit of provisional application 60/072,987 filed Jan. 21, 1998.

BACKGROUND OF THE INVENTION

Bone is a dynamic tissue, and homeostasis in the adult skeleton requires a balance between bone resorption and bone formation. Osteoclasts and osteoblasts play a key role in this balance, with osteoclasts initiating bone resorption and osteoblasts synthesizing and depositing new bone matrix. Imbalances in bone homeostasis are associated with such conditions as osteoporosis, Paget's disease, and hyperparathyroidism.

The activities of osteoclasts and osteoblasts are regulated by complex interactions between systemic hormones and the local production of growth factors and cytokines. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts (The Calcitonins-Physiology and Pharmacology Azria (ed.), Karger, Basel, Su., 1989), with a resultant decrease in the amount of calcium released by bone into the serum. This inhibition of bone resorption has been exploited, for instance, by using calcitonin as a treatment for osteoporosis, a disease characterized by a decrease in the skeletal mass often resulting in debilitating and painful fractures. Calcitonin is also used in the treatment of Paget's disease where it provides rapid relief from bone pain, which is frequently the primary symptom associated with this disease. This analgesic effect has also been demonstrated in patients with osteoporosis or metastatic bone disease and has been reported to relieve pain associated with diabetic neuropathy, cancer, migraine and post-hysterectomy. Reduction in bone pain occurs before the reduction of bone resorption.

Salmon calcitonin has been shown to be considerably more effective in arresting bone resorption than human forms of calcitonin. Several hypotheses have been offered to explain this observation: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites.

Despite the advantages associated with the use of salmon calcitonin in humans, there are also disadvantages. For treatment of osteoporosis, for instance, the average cost can exceed $75 a week and involve daily prophylactic administration for 5 or more years. In the United States, calcitonin must be administered by injection, and since the disease indications for this drug are not usually life threatening, patient compliance can be low. Resistance to calcitonin therapy may occur with long-term use. What triggers this resistance or "escape phenomenon" is unknown (see page 1093, *Principles of Bone Biology*, Bilezikian et al., (eds.) Academic Press, NY; Raisz et al., *Am. J. Med.* 25 43:684–90, 1967; McLeod and Raisz, *Endocrine Res. Comm.*8:49–59, 1981; Wener et al., *Endocrinology.* 90:752–9, 1972 and Tashjian et al., *Recent Prog. Horm. Res.* 34:285–303, 1978). Use of calcitonin mimetics, either in place of native calcitonins or in rotation with native calcitonins, would help avoid resistance to such treatment during long-term use. In addition, some patients develop antibodies to non-human calcitonin, calcitonin mimetics would be useful for such patients.

What is needed in the art are alternative methods of inhibiting bone resorption. The present invention fulfills these and other needs.

SUMMARY OF THE INVENTION

The present invention provides isolated compounds that are useful as calcitonin mimetics. As used herein, the term "calcitonin mimetic" refers to a compound with the ability to mimic the effects generated by calcitonin's interaction with its receptor and its signal transduction pathway and, by such interaction, stimulate G-protein-mediated activation by adenyl cyclase.

Within one aspect the invention provides a compound of formula I:

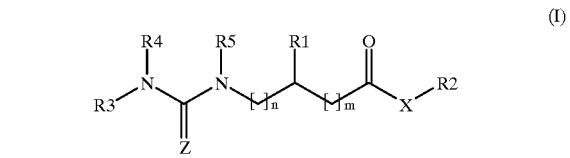

wherein R1 and R2 are each members independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; R3 is a 2,5 disubstituted aryl; R4 and R5 are each independently selected from the group consisting of hydrogen and alkyls having from 1 to 6 carbon atoms, or taken together from a ring selected from the group consisting of saturated or unsaturated five-member rings, saturated or unsaturated six-member rings and saturated or unsaturated seven-member rings; Z and X are each independently selected from the group NH, O, S, or NR, wherein R is a lower alkyl group of from 1 to 6 carbon atoms; n and m are each independently an integer from 0 to 6. Within one embodiment R1 is selected from the group consisting of phenyl, substituted phenyl, benzyl, substituted benzyl, naphthylmethyl, substituted naphthylmethyl, indolymethyl, and substituted indolymethyl; R2 is selected from the group consisting of alkyls of from 1 to 6 carbon atoms, alkenyls of from 1 to 6 carbon atoms, benzyl, substituted benzyl, naphthylmethyl, and substituted naphthylmethyl; wherein substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and R4 and R5 are hydrogen; Z is O; and X is NH. Within a related embodiment R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl; and R2 is ethyl, allyl, benzyl or 2-naphthylmethyl. Within another embodiment the compound has the formula:

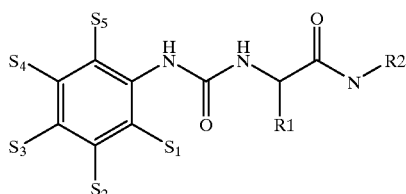

wherein, R1 and R2 are each independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and S1, S3 and S4 are each independently selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl. S2 and S5 are each independently alkyl or aryl. Within one embodiment R1 is selected from the group consisting of phenyl, substituted phenyl, benzyl, substituted benzyl, naphthylmethyl, substituted naphthylmethyl, indolymethyl, and substituted indolymethyl; R2 is selected from the group consisting of alkyls having from 1 to 6 carbon atoms, alkenyls having from 1 to 6 carbon atoms, benzyl, substituted benzyl, naphthylmethyl, and substituted naphthylmethyl; wherein the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl and S2 and S5 are t-butyl. Within a related embodiment R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl; R2 is ethyl, allyl, benzyl or 2-naphthylmethyl; and S2 and S5 are t-butyl.

Within another aspect, the invention provides a pharmaceutical composition comprising an effective amount of a compound as described above in a pharmaceutically acceptable carrier.

Within another aspect the invention provides a method for treating a bone-related disorder, comprising administering to a subject suffering from such disorder an effective amount of calcitonin mimetic compound as described above. Within a related embodiment the bone-related disorder is selected from the group consisting of osteoporosis, Paget's disease, hyperparathyroidism, osteomalacia, periodontal applications (bone loss), hypercalcemia of malignancy and hypercalcemia of infancy.

Within another aspect the invention provides a method of inhibiting bone resorption comprising administering to a subject in need of such inhibition an effective amount of a calcitonin mimetic compound as described above.

Within yet another aspect the invention provides a method for providing an analgesic effect comprising administering to a subject in need of such an effect an effective amount of a calcitonin mimetic compound as described above. Within a related embodiment the analgesic effect provides relief from bone pain.

Within another aspect the invention provides a method for treating conditions associated with inhibiting gastric secretion comprising administering to a subject in need of such inhibition an effective amount of a calcitonin mimetic compound as described above. Within a related embodiment the conditions associated with inhibiting gastric secretion is a gastrointestinal disorder.

These and other aspects of the invention will become evident upon reference to the following detailed description and the attached drawings.

DETAILED DESCRIPTION OF THE INVENTION

Abbreviations

The following abbreviations are used herein: Boc, t-butoxycarbonyl; DCM, dichloromethane; DME, dimethoxyethane; DMF, dimethylformamide; EtOAc, ethyl acetate; Fmoc, fluorenylmethoxycarbonyl; TFA, trifluoroacetic acid.

All references cited herein are incorporated by reference in their entirety.

The calcitonin mimetics which are useful in the present invention are those compounds with the ability to mimic the interaction of calcitonin with its receptor and, by such mimicry, to stimulate G-protein-mediated activation of adenyl cyclase or activation of CRE by an alternative signal transduction pathway. These mimetics are represented by the general formula:

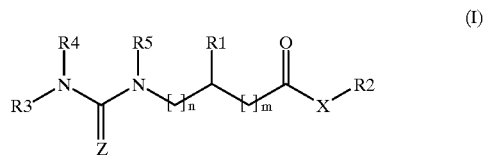

(I)

In this formula, R1 and R2 are each independently hydrogen, alkyl groups having from 1 to 6 carbon atoms, alkenyl groups having from 1 to 6 carbon atoms, an aryl group, or alkylaryl groups, where the alkyl portion may have 1 to 6 carbon atoms and the aryl portion represents an aryl group, a substituted aryl group, a carbocyclic ring, a substituted carbocyclic ring, a heterocyclic ring, a substituted heterocyclic ring, or combinations thereof. The combinations can be fused or covalently linked. In certain preferred embodiments R1 is substituted or unsubstituted phenyl, benzyl, naphthylmethyl or indolymethyl. R2 is an alkyl or alkenyl having from 1 to 6 carbon atoms, substituted or unsubstituted benzyl or naphthylmethyl. In certain particularly preferred embodiments R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl. R2 is ethyl, allyl, benzyl, or 2-naphthylmethyl.

R3 represents substituted and unsubstituted aryl groups, carbocyclic rings, heterocyclic rings, or combinations thereof. The combinations can be fused or covalently linked. Within certain preferred embodiments R3 is a 2,5 disubstituted aryl. Preferably the substitutions are aryl or alkyl. Within a preferred embodiment R3 is 2,6-di-t-butyl-phenyl.

R4 and R5 are each independently hydrogen, alkyl groups having from 1 to 6 carbon atoms. Within certain embodiments R4 and R5 can be joined together to form a ring which is a four-, five-, six- or seven-member ring, saturated or unsaturated. For those embodiments in which the ring is unsaturated, the ring can be an heteroaromatic ring (e.g., pyrimidyl, imidazyl). Within certain preferred embodiments R4 and R5 are hydrogen.

Z and X each independently represent either NH, NR, O, or S, in which R is a lower alkyl group of from one to six carbon atoms. In preferred embodiments, z represents O and X represents NH. The symbols n and m each represent independently, integers from zero to six.

As used herein, the term "alkyl" refers to a saturated hydrocarbon radical which may be straight-chain or branched-chain (for example, ethyl, isopropyl, or t-butyl), or cyclic (for example cyclobutyl, cyclopropyl or cyclopentyl). Preferred alkyl groups are those containing 1 to 6 carbon atoms.

The term "alkenyl" refers to an unsaturated hydrocarbon radical which may be a straight-chain, branched-chain or cyclic. Examples of alkenyls include vinyl, allyl, 2-butenyl, 3-butenyl, 2-pentenyl, 3-pentenyl, 3-pentenyl, 4-pentenyl, 2-hexenyl, 3-hexenyl, 4-hexenyl and 5-hexenyl, as well as dienes and trienes of straight, branched or cyclic chains and the like. Preferred alkenyl groups are those containing 1 to 6 carbon atoms.

The term "aryl" refers to an aromatic substituent which may be a single ring or multiple rings which are fused together, linked covalently or linked to a common group such as an ethylene or methylene moiety. The aromatic rings may each contain heteroatoms, preferred heteroatoms are N, S or O. Examples of aryl groups include phenyl, benzyl, naphthyl, biphenyl, diphenylmethyl, 2,2-diphenyl-1-ethyl, thienyl, pyridyl and quinoxalyl. Additionally, the aryl groups may be attached to other parts of the molecule at any position on the aryl radical which would otherwise be occupied by a hydrogen atom (such as, for example, 2-pyridyl, 3-pyridyl and 4-pyridyl).

Heterocyclic rings contain at least one heteroatom selected from N, O and S. Examples of carbocyclic and heterocyclic rings include cyclohexyl, cyclohexenyl, piperazinyl, pyrazinyl, morpholinyl, imidazolyl, triazolyl and thiazolyl.

The terms "substituted alkyl", "substituted alkenyl", "substituted alkylaryl", "substituted aryl", "substituted carbocyclic ring", "substituted heterocyclic ring" "substituted phenyl", "substituted benzyl", "substituted naphthylmethyl" and "substituted indolymethyl" refer to the above alkyl, alkenyl, alkylaryl, carbocyclic ring, heterocyclic ring, aryl, phenyl, benzyl, naphthylmethyl and indolylmethyl groups substituted by one or more, preferably one, halogen, haloalkyl, hydroxy, aryloxy, benzyloxy, alkoxy, haloalkoxy, amino, monoalkylamino, dialkylamino, acyloxy, acyl, alkyl and aryl. Examples include 4-ethoxybenzyl, 1-ethyl-indolylmethyl, 4-alloxybenzyl, 1-allyl-indolylmethyl, 4-chlorobenzyl, 4-flurobenzyl, 4-iodobenzyl or 2-naphthylmethyl.

All numerical ranges in this specification and claims are intended to be inclusive of their upper and lower limits.

In one group of preferred embodiments, the calcitonin mimetics are represented by the formula:

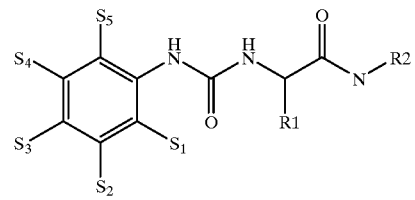

In this formula, the symbols R1 and R2 have the meaning provided above. The symbols S1, S3 and S4 each independently represent a substituent on the attached aromatic ring which is hydrogen, halogen, haloalkyl, hydroxy, aryloxy, benzyloxy, alkoxy, haloalkoxy, amino, monoalkylamino, dialkylamino, acyloxy, acyl, alkyl and aryl. The symbols S2 and S3 each represent an aryl or alkyl. In certain preferred embodiments R1 is substituted or unsubstituted phenyl, benzyl, naphthylmethyl or indolymethyl. R2 is an alkyl or alkenyl having from 1 to 6 carbon atoms, substituted or unsubstituted benzyl or naphthylmethyl. In certain particularly preferred embodiments, S5 and S2 are t-butyl, R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl and R2 is ethyl, allyl, benzyl, or 2-naphthylmethyl.

The calcitonin mimetics used in the present invention can be prepared using commercially available materials. A general synthetic scheme for preparing molecules of Formula I wherein R4 and R5 are hydrogen, using methodologies known in the art, is provided herein.

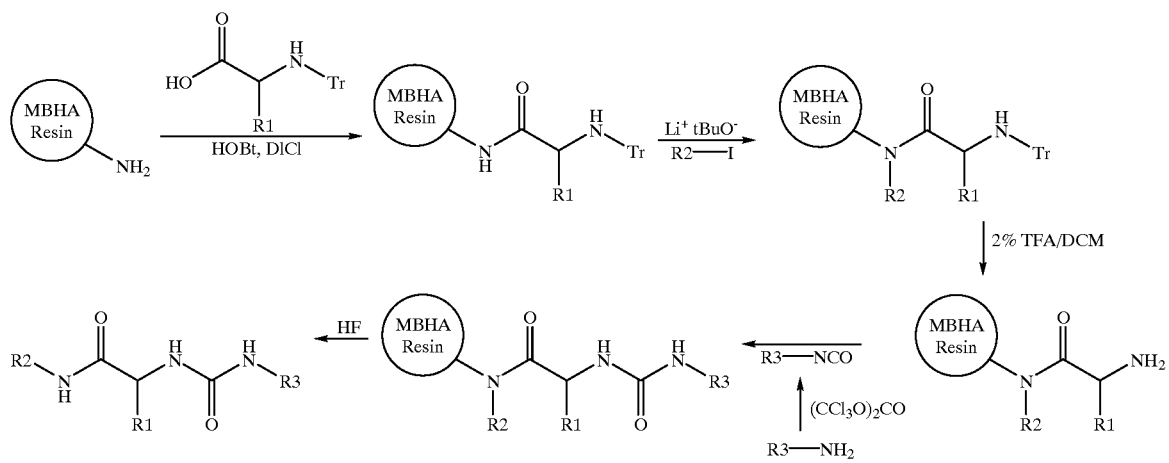

In a typical preparation, 100 mg of p-methylbenzhydrylamine (MBHA) resin (0.81 meq/g, 100–200 mesh) was contained within a sealed polypropylene mesh packet. Following neutralization with 5% diisopropylethylamine (DIEA) in dichloromethane (DCM), the resin was washed with DCM. The first protected amino acid was coupled using hydroxybenzotriazole (HOBt) and diisopropylcarbodiimide (DICI) in DMF. Following removal of the amino protecting group, the mesh packet was shaken overnight in a solution of 0.1 M trityl chloride in DCM/DMF (9:1) in the presence of DIEA. Completeness of the trityl coupling was verified using the bromophenol blue color test as described in Krchnak et al., (*Coll. Czech. Chem. Commun.* 53:2542, 1988, and repeated as necessary.

N-alkylation was then performed by treatment of the resin packet with 1 M lithium t-butoxide in THF (20×) for 15 min, as described by Drner, et al., (*Bioorg. Med. Chem.* 4:709, 1996). Excess base was then removed by decantation, followed by addition of the individual alkylating agent in DMSO (20×, 0.1M). The solution was vigorously shaken for 2 h at room temperature. This step is normally repeated three times for methyl iodide, and five times for the other alkylating agents. Small aliquots of the resin can be cleaved to determine the completeness of this step. The trityl group was removed with 2% TFA in DCM (2×10 min).

The isocyanate of the incoming primary amine (or aniline) was performed by slowly adding a solution of the primary amine (0.3M in DCM, 24× over the resin substitution) and DIEA (48×) dropwise to solution of 0.1M triphosgene (8×) in DCM. It is known in the art that the reaction does not proceed through the isocyanate for secondary amines. The packet was washed, neutralized and the isocyanate solution added and shaken for 1 hour at RT. Following decantation, the isocyanate solution was quenched with 10% $NH_3$ in DMF. The resin was washed with DCM, 0.05% $NH_3$ in DMF, MeOH, DCM, and MeOH.

The product was cleaved from the resin with anhydrous HF by the procedures of Houghten et al., (*Int. J. Pep. Prot. Res.* 27:673, 1986), in the presence of anisole. The product was extracted with 50% ACN/$H_2O$ and lyophilized, followed by relyophilization from 50% acetonitrile.

The compounds of the invention can be administered to warm blooded animals, including humans, to mimic the interaction of calcitonin with its receptor in vivo. Within one aspect, calcitonin mimetics of the present invention are contemplated to be advantageous for use in therapeutic defects for which calcitonin is useful. In particular, the calcitonin mimetics are useful for the regulation of bone metabolism and reduction of serum calcium. The calcitonin mimetics of the invention can be administered to warm blooded animals, including humans, to mimic the interaction of calcitonin with its receptor in vivo. Thus, the present invention encompasses methods for therapeutic treatment of bone-related disorders. Such bone-related disorders include, but are not limited to, osteoporosis, Paget's Disease, hyperparathyroidism, osteomalacia, periodontal defects (bone loss), hypercalcemia of malignancy, idiopathic hypercalcemia of infancy, and other related conditions. Calcitonin mimetics are also contemplated to be advantageous as analgesics, in particular for relief of bone pain. Calcitonin mimetics are further contemplated to be advantageous in inhibiting bone resorption. The calcitonin mimetics of the present invention can also be used to inhibit gastric secretion in the treatment of acute pancreatitis and gastrointestinal disorders. The methods of the present invention may be used to treat these conditions in their acute or chronic stages.

Pharmaceutically or therapeutically effective amounts of calcitonin mimetics of the present invention can be formulated with pharmaceutically or therapeutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and maybe provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the calcitonin mimetic. Such slow release systems are applicable to formulations, for example, for oral, topical and parenteral use. The term "pharmaceutically or therapeutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in Remington: The Science and Practice of Pharmacy, Gennaro, ed., Mack Publishing Co., Easton, Pa, 19th ed., 1995. Preferably such compounds would be administered orally or parenterally.

As used herein, a "pharmaceutically or therapeutically effective amount" of such a calcitonin mimetic is an amount sufficient to induce a desired biological result. The result can be alleviation of the signs, symptoms, or causes of a disease, or any other desired alteration of a biological system. For example, an effective amount of a calcitonin mimetic is that which provides either subject relief of symptoms or an objectively identifiable improvement as noted by the clinician or other qualified observer. In particular, such an effective amount of a calcitonin mimetic results in reduction in serum calcium, inhibition of bone resorption, inhibition of gastric secretion or other beneficial effect. Effective amounts of the calcitonin mimetics can vary widely depending on the disease or symptom to be treated. The amount of the mimetic to be administered, and its concentration in the formulations, depends upon the vehicle selected, route of administration, the potency of the particular mimetic, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Estimation of appropriate dosages effective for the individual patient is well within the skill of the ordinary prescribing physician or other appropriate health care practitioner. As a guide, the clinician can use conventionally available advice from a source such as the Physician's Desk Reference, 48th Edition, Medical Economics Data Production Co., Montvale, N.J. 07645–1742 (1994). Typically a dose will be in the range of 0.1–100 mg/kg of subject. Preferably 0.5–50 mg/kg. Doses for specific compounds may be determined from in vitro or ex vivo studies on experimental animals. Concentrations of compounds found to be effective in vitro or ex vivo provide guidance for animal studies, wherein doses are calculated to provide similar concentrations at the site of action.

Well established animal models are available to test in vivo efficacy of calcitonin mimetics. For example, the hypocalcemic rat model can be used to determine the effect of synthetic calcitonin mimetics on serum calcium, and the ovariectomized rat or mouse can be used as a model system for osteoporosis. Bone changes seen in these models and in humans during the early stages of estrogen deficiency are qualitatively similar. Calcitonin has been shown to be an effective agent for the prevention of bone loss in ovariectomized humans and also in rats (Mazzuoli, et al., *Calcif. Tissue Int.* 47:209–14, 1990; Wronski, et al., *Endocrinology* 129:2246–50, 1991).

Only those compounds which retain calcitonin-like activity, as assayed by a CRE-luciferase assay, for example, are within the scope of this invention. The calcitonin receptor is a member of the G-protein receptor family and transduces signal via activation of adenylate cyclase, leading to elevation of cellular cAMP levels (Lin, et al., *Science* 254:1022–4, 1991). This assay system exploits the receptor's ability to detect other molecules, not calcitonin, that are able to stimulate the calcitonin receptor and initiate signal transduction.

Receptor activation can be detected by: (1) measurement of adenylate cyclase activity (Salomon, et al., *Anal. Biochem.* 58:541–8, 1974; Alvarez and Daniels, *Anal. Biochem.* 187:98–103, 1990); (2) measurement of change in intracellular cAMP levels using conventional radioimmunoassay methods (Steiner, et al., *J. Biol. Chem.* 247:1106–13, 1972; Harper and Brooker, *J. Cyc. Nucl. Res.* 1:207–18, 1975); or (3) use of a cAMP scintillation proximity assay (SPA) method (Amersham Corp., Arlington Heights, Ill.). While these methods provide sensitivity and accuracy, they involve considerable sample processing prior to assay, are time consuming, may involve the use of radioisotopes, and would be cumbersome for large scale screening assays.

An alternative assay system (described in WO96/31536) involves selection of substances that are able to induce expression of a cyclic AMP response element (CRE)-luciferase reporter gene, as a consequence of elevated cAMP levels or other signaling pathways, such as stimulation of $Ca^{++}/Ip_3$ pathway leading to CRE induction, in cells expressing a calcitonin receptor, but not in cells lacking calcitonin receptor expression. Such cells could include, for example, Boris/KS10-3 (expressing hamster calcitonin receptor and a CRE-luciferase reporter gene in baby hamster kidney cells (BHK 570 cells)) or Hollex 1 or Hollex 2 (expressing human calcitonin receptor and a CRE-luciferase reporter gene in BHK cells, as described in WO96/31536) or KZ10-20-48/pLJ6-4-25, which expresses the human glucagon receptor and a CRE-luciferase reporter gene in BHK cells. The human glucagon receptor is another member of the C-protein-coupled receptor that transduces signal through adenylate cyclase-mediated elevation of cAMP. PTH can be used as a control as well.

This CRE-luciferase assay measures the end result of a multi-step signal transduction pathway triggered when a calcitonin mimetic stimulates the G-coupled calcitonin receptor. The complexity of this pathway provides multiple mechanisms for induction of luciferase transcription at points that are downstream of the calcitonin receptor, and therefore may not be calcitonin receptor-specific (e.g., forskolin's direct activation of adenylate cyclase). Any response triggered by non-specific inducers is eliminated by counter screening using the calcitonin receptor-negative cell lines described above.

The foregoing description and the following examples are offered primarily for illustration and not as limitations. It will be readily apparent to those of ordinary skill in the art that the operating conditions, materials, procedural steps and other parameters of the system described herein may be further modified or substituted in various ways without departing from the spirit and scope of the invention. The invention is further illustrated by the following non-limiting examples.

EXAMPLES

Example 1

Preparation of Calcitonin Mimetics: Urea of Aniline and L-Leucine Methylamide

Preparation of Trityl-leucine Amide Resin

In the preparation of the urea of aniline and leucine methyl amide, 100 mg of p-methylbenzhydrylamine (MBHA) resin (0.81 meq/g, 100–200 mesh) was contained within a sealed polypropylene mesh packet as used in simultaneous multiple synthesis as described in Houghten, (*Proc. Natl. Acad. Sci. USA* 82:5131, 1985). Following neutralization (1 min) with 5% diisopropylethylamine (DIEA) in dichloromethane (DCM) (3×5 ml), the resin was washed with DCM (3×5 ml). The resin packet was added to a solution of tert-butyloxycarbonyl-L-leucine (Boc-Leu) (111 mg, 0.48 meq) and 1-hydroxybenzotriazole (65 mg, 0.48 meq) in dimethylformamide (DMF) (2.4 ml) in a 10 ml polypropylene bottle. Following addition of 2.4 ml 0.2 M diisopropylcarbodiimide (DICI) in DMF, the resin was shaken on a reciprocation shaker for 1.5 h. The resin was then washed with DMF (3×5 ml) and DCM (3×5 ml). The Boc protecting group was then removed by treatment with 55% trifluoroacetic acid in DCM for 30 min. The resin was then washed with DCM (2×5 ml), isopropanol (IPA, 3×5 ml), DCM (3×5 ml), neutralized with 5% DIEA in DCM (3×5 ml), and washed with DCM (2×5 ml). The resin packet was then shaken overnight (16 h) in 5 ml of 0.1 M trityl chloride in DCM/DMF (9:1) in the presence of DIEA. Completeness of the trityl coupling was verified using the bromophenol blue color test as described in Krchnak et al., (*Coll. Czech. Chem. Commun.* 53:2542, 1988), and repeated as necessary.

N-Methylation of trityl-leucine Amide Resin

N-methylation was then performed by treatment of the resin packet with a solution of 3.2 ml 0.5 M lithium t-butoxide (LiOtBu) in THF for 15 min, as described by D rner, et al., (*Bioorq. Med. Chem.* 4:709, 1996). Excess base was then removed by decantation, followed by addition of a solution of 0.3 ml methyl iodide in 3.2 ml dimethylsulfoxide (DMSO). The solution was shaken for 2 hours at room temperature. The solution was then removed, washed with THF (1×5 ml) and the LiOtBu/methyl iodide treatment repeated. Following removal of the solution, the resin was washed with DMF (3×5 ml), IPA (2×5 ml), DCM (3×5 ml). The trityl group was removed by two treatments (10 min) with 2% TFA in DCM (5 ml). The resin was then washed with DCM (2×5 ml), IPA (3×5 ml) and DCM (3×5 ml).

Preparation of the Urea of Aniline and Leucine Methylamide Resin

The resin packet was neutralized (1 min) with 5% DIEA in DCM (3×5 ml), and washed with DCM (2×5 ml). The isocyanate of aniline was then performed by slowly adding a solution of aniline (0.176 ml) in DCM (6.5 ml) and DIEA (0.678 ml) dropwise with stirring to a solution of triphosgene (193 mg) in DCM (6.5 ml). The resin packet was added to the isocyanate solution and shaken for 1 hour at room temperature. Following decantation, the resin was washed with DCM (1×5 ml), 0.05% NH3 in DMF (2×5 ml), IPA (1×5 ml), DCM (1×5 ml), and methanol (1×5 ml). The resin was then dried under high vacuum overnight.

Cleavage of the Urea from the Resin

The product was cleaved from the resin using 5 ml of anhydrous HF for 1.5 h at 0° C. by the procedures of Houghten et al., (*Int. J. Pep. Prot. Res.* 27:673, 1986). The product was extracted with 50% acetonitrile(ACN)/$H_2O$ (2 ×5 ml) and lyophilized, followed by relyophilization from 50% ACN/$H_2O$ (5 ml). 13.5 mg crude product (85% purity by RP-HPLC) having the expected molecular weight of 263 daltons was obtained.

Example 2

This example provides in vitro, ex vivo, and in vivo assays which can be used to evaluate compounds described herein for their use in therapeutic applications.

Assays for Calcitonin Mimetic Activity
CRE-Luciferase Assay Method for Calcitonin Mimetics Human calcitonin receptor-positive and receptor-negative BHK-570 (Baby Hamster Kidney) cell lines were maintained by serial passage in growth medium (DMEM supplemented with 10% heat-inactivated fetal calf serum (HI-FCS), 2 mM L-glutamine, 1 mM sodium pyruvate, 250 nM MTX, and 1 mg/mL G418). On the day prior to assay, cells were trypsinized, adjusted to $2.5 \times 10^5$ cells/ml in growth medium, plated in opaque white Dynatech Microlite microtiter tissue culture plates at 50 μL/well, and grown overnight to confluence (37° C., 5% $CO_2$ atmosphere).

Test substances were prepared in DMSO or 10% DMF at 100 times the final desired assay concentration. At the time of assay, test substances were diluted into assay medium to 100, 50, 25, and 12.5 μg/ml in DMEM supplemented with 10% HI-FCS, 2 mM L-glutamine, 1 mM sodium pyruvate and 20 mM Hepes, pH 7.25, then 50 μl/well was added to assay plates for final assay concentrations of 50, 25, 12.5 and 6.25 μg/ml in 1% DMSO (or 0.1% DMF). Controls were included on each plate: untreated wells (basal), 25 mM forskolin, and 100 nM human calcitonin. DMSO or DMF was included in control wells at a concentration equal to that in test samples (not to exceed a final assay concentration of 2% DMSO or 0.5% DMF, with a preferred maximum of 1% DMSO or 0.1% DMF).

Plates were incubated for 3 to 8 hours (4 hours preferred) at 37° C. in an atmosphere of 5% $CO_2$. Following induction, luciferase activity was measured using a Promega luciferase assay kit (E1500) according to the assay kit protocol (Promega Corp., Madison, Wis.). Briefly, assay medium was removed and cells were washed once with phosphate buffered saline (PBS). After the wash, 25 μl of lysis buffer was added to each well, and the plates were incubated for 15 minutes at room temperature. Fifty microliters of Luciferase Assay Substrate (Promega, Corp.) was added to each well and the plates were transferred to a Labsystems Lumiscan microtiter luminometer (Labsystems Inc., Morton Grove, Ill.). The amount of luminescence (relative light units, RLU) was determined following a 0.1 second/well integration of signal. Basal (uninduced) luciferase signal was subtracted from all measurements, and the luciferase signal induced by test samples was expressed as a percentage of the signal in the calcitonin and forskolin controls. Specificity of the luciferase induction for calcitonin receptor-positive cell lines was determined by comparing the percent control values in the calcitonin receptor-positive line (Hollex-1) to those observed in the calcitonin receptor-negative cell line (KZ10-20-48/Zem 228) and the PTH receptor-positive cell line (KZ10-20-48/PTH-20) described below. Samples inducing a signal over the basal level were selected for further characterization, see Table 1 for examples.

TABLE 1

Luciferase induction (% of maximum luciferase induction produced by CT, 100 nM)

| TPI # | R1 | R2 | 50 | 25 | 12.5 | 6.25 | 3.125 |
|---|---|---|---|---|---|---|---|
| 628-007 | $X_1$-CH2-C6H4-O-CH2CH3 | $X_2$-CH2-CH3 | 31.73 | 55.34 | 31.97 | 10.61 | 0.76 |
| 628-008 | $X_1$-CH2-(1-ethyl-indol-3-yl) | $X_2$-CH2-CH3 | 50.39 | 50.93 | 20.07 | 2.91 | −1.31 |

TABLE 1-continued
Luciferase induction (% of maximum luciferase induction produced by CT, 100 nM)
| ID | $X_1$ | $X_2$ | | | | | |
|---|---|---|---|---|---|---|---|
| 628-013 | 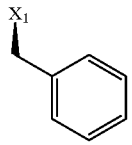 benzyl | 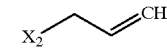 allyl | 64.26 | 69.62 | 51.62 | 17.98 | 3.51 |
| 628-015 | 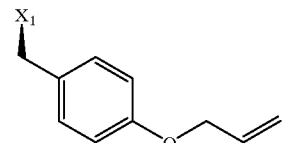 4-allyloxybenzyl | 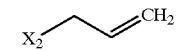 allyl | 71.49 | 72.17 | 43.2 | 14.69 | 1.62 |
| 628-016 | 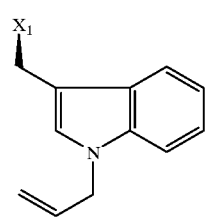 (1-allyl-1H-indol-3-yl)methyl | 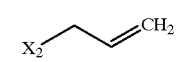 allyl | 75.76 | 80.63 | 76.44 | 43.89 | 10.72 |
| 628-022 | 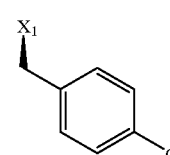 4-chlorobenzyl | 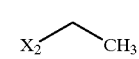 ethyl | 46.98 | 41.52 | 17.85 | 3.26 | 2.08 |
| 628-023 | 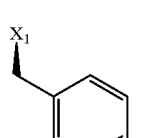 4-fluorobenzyl | 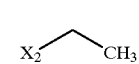 ethyl | 41.79 | 46.84 | 32.04 | 7.84 | -0.46 |
| 628-024 | 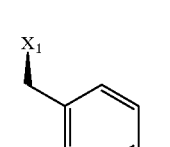 4-iodobenzyl | 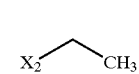 ethyl | 30.25 | 22.64 | 11.8 | 1.39 | -1.24 |
| 628-025 | 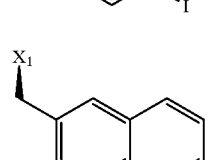 2-naphthylmethyl |  ethyl | 22.61 | 7.96 | 2.33 | 0.65 | 0.42 |
| 628-042 | 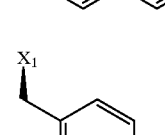 4-chlorobenzyl | 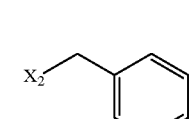 benzyl | 60.41 | 68.69 | 59.74 | 49.17 | 19.16 |
| 628-043 | 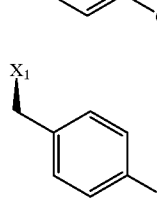 4-fluorobenzyl | 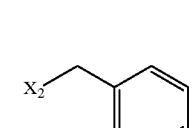 benzyl | 47.95 | 46.24 | 42.06 | 34.53 | 6.48 |

TABLE 1-continued

Luciferase induction (% of maximum luciferase induction produced by CT, 100 nM)

| TPI # | R1 | R2 | | | | | |
|---|---|---|---|---|---|---|---|
| 628-044 | 4-I-benzyl (X1) | benzyl (X2) | 30.14 | 26.23 | 29.35 | 24.08 | 10.65 |
| 628-045 | 2-naphthylmethyl (X1) | benzyl (X2) | 40.62 | 44.51 | 42.49 | 38.73 | 20.19 |
| 628-052 | 4-Cl-benzyl (X1) | 2-naphthylmethyl (X2) | 38.27 | 40.21 | 36.63 | 23.59 | 9.57 |
| 628-053 | 4-F-benzyl (X1) | 2-naphthylmethyl (X2) | 40.14 | 41.8 | 32.31 | 11.89 | 3.29 |
| 628-054 | 4-I-benzyl (X1) | 2-naphthylmethyl (X2) | 54.86 | 47.47 | 42.54 | 27.05 | 10.73 |
| 628-056 | phenyl (X1) | 2-naphthylmethyl (X2) | 37.1 | 35.6 | 28.6 | 14.7 | 4.2 |

| TPI # | R1 | R2 | Purified μg/ml | | | |
|---|---|---|---|---|---|---|
| 628-055 | 2-naphthylmethyl (X1) | 2-naphthylmethyl (X2) | 48.69 | 43.3 | 35.48 | 24.81 |
| 628-032 | 4-Cl-benzyl (X1) | allyl (X2) | 33.94 | 31.34 | 27.28 | 25.42 |

TABLE 1-continued

Luciferase induction (% of maximum luciferase induction produced by CT, 100 nM)

| ID | Structure 1 | Structure 2 | Values |
|---|---|---|---|
| 628-033 | $X_1$-CH$_2$-C$_6$H$_4$-F (para) | $X_2$-CH$_2$-CH=CH$_2$ | 33.62  31.63  27.68  14.71 |
| 628-034 | $X_1$-CH$_2$-C$_6$H$_4$-I (para) | $X_2$-CH$_2$-CH=CH$_2$ | 38.68  33.86  25.02  6.89 |
| 628-035 | $X_1$-CH$_2$-naphthyl | $X_2$-CH$_2$-CH=CH$_2$ | 52.27  46.43  43.25  34.84 |
| 628-036 | $X_1$-C$_6$H$_5$ | $X_2$-CH$_2$-CH=CH$_2$ | 10.38  8.0   6.43   4.12 |

Test substances that appear to specifically elevate luciferase expression in CT-R positive cells but not CT-R negative cells were subjected to an additional specificity check, i.e. their inability to activate other members of the G-protein coupled receptor family. The parathyroid hormone (PTH) receptor is another member of the G-protein coupled receptor family that transduces signal through adenylate cyclase mediated elevation of cAMP. The receptor negative CRE-luciferase/DHFR expressing BHK570 clone (KZ10-20-48) was transfected with the plasmid phupthr.2, encoding the cloned human PTH receptor in plasmid pHZ-1 which also contains the G418 selectable marker. Stable transfectants were selected in 250 nM MTX+1 mg/ml G418 and were screened for CRE-luciferase induction in response to 25 mM forskolin or 100 nM human PTH (Sigma) (as described in WO96/31536). Clone KZ10-20-48/PTH-20 was selected for use in specificity confirmation. This clone exhibits a 25 fold induction of luciferase in response to human PTH (EC50=0.02 nM) or forskolin (EC50=2.0 uM).

Calvarial Assay

Calvaria from 4-day old neonatal CD-1 mice (pregnant mice received from Charles River Laboratories, Wilmington, Mass.) were trimmed with fine-tipped scissors to leave the parietal regions, including the sagittal suture. These trimmed bones were placed singly per well into 6-well cell culture cluster plates (Costar, Pleasanton, Calif.) with 1 ml/well of Dulbecco's Minimum Essential Medium, 4.5 ug/ml glucose (DMEM, BioWhittaker, Walkersville, Md.) or Basal Eagle's Medium with Earle's salts (EMEM, Gibco/BRL, Grand Island, N.Y.) and 0.29 mg/ml L-glutamine, 1 mM sodium pyruvate, 15% heat-inactivated horse serum, and antibiotics (penicillin-G 50 µg/ml, streptomycin 50 µg/ml, and neomycin 100 µg/ml). Calvaria were rocked gently (RedRocker™, model PR50-115V, Hoefer, San Francisco, Calif. or Labline Rocking Shaker, model 4635, Labline Instruments, Melrose Park, Ill.) at 37° C. in a 5% $CO_2$ humidified incubator for 24 hours preincubation.

Following preincubation, medium was removed and replaced with 1.5 ml/well of growth medium containing 1 nM parathyroid hormone (PTH) 1–34 (Sigma) to stimulate bone resorption. For evaluation of the ability of calcitonin mimetics to inhibit PTH induced bone resorption, mimetic compounds in DMSO were added to the growth medium at concentrations ranging from 1–400 µg/ml (final assay concentration of DMSO less than or equal to 1%). In each experiment human calcitonin (0.02–20 nM, 0.2–2 nM preferred) was added to PTH treated bones as a positive control. Control wells that did not receive PTH, human calcitonin or calcitonin mimetic were included for determination of calcium release from untreated bones. All control wells contained a final assay concentration of DMSO equal to that present in calcitonin mimetic treated wells.

Five bones were included in each sample group. Bones were incubated for 72 hours following PTH addition to allow resorption of bone to occur. Observations were made of the general appearance, healthiness and number of cells that migrate from the calvaria during the incubation as a possible indication of cell toxicity. Calvaria to be examined histologically were transferred to glass scintillation vials containing 10 ml of 10% neutral buffered formalin.

The medium was removed from the wells, and total calcium measurements were made using a Nova 7/7+7 Electrolyte Analyzer or Nova CRT 10 analyzer (Nova Biomedical, Waltham, Mass.) according to the manufacturer's specifications. Induction of bone resorption by PTH is seen as an increase in the concentration of calcium in the growth medium due to degradation of the bone matrix. Human calcitonin and biologically active calcitonin mimetics inhibit this bone resorptive process as demonstrated by a lowering of the calcium in growth medium as compared to bones treated with PTH alone.

Calvaria Histology

To confirm the findings in the calvarial bone resorption assay employing calcium release from culture mouse calvariae, selected bones were fixed in 10% neutral buffered formalin and demineralized in 5% formic acid with 5% formalin. The bones were dehydrated through an ascending series of ethanol concentrations, infiltrated in glycol methacrylate, and embedded using a JB-4 embedding kit (PolySciences, Warrington, Pa.) (Liu, et al., *J. Bone Mineral Res.* 5:973–82, 1990). When necessary, an alternative embedding method (paraffin embedding) was used to speed lip the embedding process. Cross sections of calvariae cut at 5 μm were obtained and stained for tartrate-resistant acid phosphatase (TRAP) activity and counterstained with methyl green and thionin for cell morphology (Liu, et al., ibid.). Osteoclasts were identified by TRAP stain, multinucleation, large cell size, and irregular cell shape. The number of osteoclasts were counted from endocranial and ectocranial bone surfaces and expressed as number/mm perimeter. The size of all the osteoclasts counted was also measured using a Bone Morphometry program (Liu, et al., ibid.; Bain, et al., *J. Bone Miner. Res.* 8:435–42, 1993). This histomorphometric method demonstrated increases in the number and size of osteoclasts due to human parathyroid hormone (PTH 1–34) treatment. This PTH-induced increase was suppressed by treatment with human calcitonin.

Calcitonin mimetic compounds were evaluated in a similar fashion for their ability to suppress PTH-induced increases in osteoclast number and size (Table 2). Cell toxicity (or death) was also evaluated by the appearance of pyknotic nuclei in a small number of bone cells. With an increased level of toxicity, a further increase in the number of these pyknotic nuclei, detachment of cells from bone surfaces, and losses of cytoplasmic stain and cell boundaries were observed. The osteocytic space also appeared empty.

TABLE 2

Effect of Calcitonin Mimetics on PTH-
Induced Bone Resorption in Mouse Calvariae Release of PTH
Induced Ca++

| Calcitonin Mimetic | IC50 (μg/ml) | Histology |
|---|---|---|
| 628-033 | 30 | Decreases in bone destruction by PTH, Oc size and # |
| 628-035 | 23 | Decreases in bone destruction by PTH, Oc size and # |
| 628-055 | 14 | Decreases in bone destruction by PTH, Oc size and # |

Oc = Osteoclast
For comparative purposes, the IC50 for human calcitonin is about 0.2 to 0.5 nM.

There was no apparent toxicity or tissue necrosis detected based on histological observation of calvaria treated with up to 50 ug/ml of compound.

Induction of Hypocalcemia in Rats

This assay is based on the in vivo acute effect of calcitonin on osteoclasts, which causes rapid retraction of osteoclasts from bone surface (typically within 30 minutes) and which results in decreased bone resorption. See Mills, et al., in Endocrinology 1971 —*Proceedings of the Third International Symposium*, Taylor (ed), Heinemann Medical, London, pp. 79–88 (1972) and Singer, et al., *Clin. Endocrinol.* 5 (Supp) :333s-40s, 1976. The assay method was modified from the method described by Sturtridge and Kumar, *Lancet* 545:725–6, 1968. For the assay of hypocalcemic activity, weanling male Holtzman Sprague-Dawley rats (22 days old) are infused with vehicle (PBS with 1 mM HCl and 0.1% BSA), calcitonin or calcitonin mimetics through the tail vein. One hour later, blood samples are collected by orbital sinus puncture to determine serum levels of calcium. A decrease in serum calcium indicates a hypocalcemic response. The hypocalcemic response is dose-dependent as determined using salmon calcitonin (0.5, 2.5, 5, 50 and 100 ng/rat) in this model.

Inhibition of PTH-induced Hypercalcemia in TPTX Rats

Continuous PTH infusion is associated with extensive destruction and severe hypercalcemia in thyroparathyroidectomized (TPTX) rats. See Thompson, et al., *Proc. Natl. Acad. Sci. USA* 85:5673–7, 1988. An animal model has been successfully established. See Liu, et al., *J. Bone Mineral Res.* 11 (Suppl. 1) :S206, 1996. For in vivo assay, male Sprague-Dawley rats (weighing about 150 g) are thyroparathyroidectomized and the success of surgery is determined by measuring the levels of serum calcium. Animals which are successfully operated on (serum calcium levels less than 8 mg/dl) are maintained on a low calcium diet (0.02% Ca and 0.6% P, ICN special diet) and infused s.c. with vehicle (PBS with 1 mM HCl and 0.1% BSA), PTH (75 ug human PTH 1–34/kg body weight/day), PTH+calcitonin (salmon calcitonin 50 U/kg body weight/day), or PTH+calcitonin mimetic via Alzet osmotic minipumps (Model 1003D, Alza Corp., Palo Alto, Calif.). Two days after infusion, animals are sacrificed and blood samples are collected to determine if the hypercalcemic response induced by PTH is inhibited by co-administration of calcitonin or calcitonin mimetic. Additionally, tibial and kidney samples are collected to determine osteoclastic bone resorption and nephrocalcinosis, respectively, and to confirm the findings in serum chemistry. Severe hypercalcemia induced by PTH has been shown to be accompanied by increases in the number and size of osteoclasts, extensive bone destruction, and calcification in kidneys (nephrocalcinosis) following only two days of treatment (see, Liu, et al., ibid.) The serum, bone and kidney changes were attenuated by co-administration of CT.

Bone Loss Induced by Combined Ovariectomy and Immobilization in Rats

Estrogen deficiency and immobilization both induce bone loss in humans and in experimental animals. The combined effects cause severe osteopenia. See, Strachan, et al., *J. Bone Mineral Res.* 11(Suppl. 1) :S456, 1996. A few studies have also shown that calcitonin is effective at reducing bone loss associated with combined ovariectomy and immobilization. See, Hayashi, et al., *Bone* 10:25–8, 1989 and McSheehy, et al., *Bone* 16:435–44, 1995. Slightly modified procedures were recently used to reproduce those results and demonstrate that calcitonin is very effective at reducing bone loss associated with the combined surgery, when evaluated by pQCT or histomorphometry in rats (see, Strachan, et al., ibid.).

For induction of bone loss, 2-month old Sprague-Dawley rats (weighing about 200 g) are ovariectomized and immobilized by neurotomy of the sciatic nerve in the left hind limb. The immobilized animals are treated with vehicle (PBS with 1 mM HCl and 0.1% BSA), calcitonin (15 U/kg body weight/day),or calcitonin mimetics for 6 weeks. Calcein injections (15 mg/kg body weight/day) are given i.p. at 9 and 2 days prior to sacrifice. Bone histomorphometry is performed as previously described (see, Liu, et al., *J. Bone Mineral Res.* 5:973–82, 1990) to determine the effects of calcitonin and calcitonin mimetics.

Calvarial Assay to Determine Calcitonin Escape

Calvaria from 4-day old neonatal CD-1 mice (pregnant mice received from Charles River Laboratories) are trimmed with fine-tipped scissors to leave the parietal regions, including the sagittal suture. These trimmed bones are placed singly per well into 6-well culture cluster plates (Costar) with 1 ml/well of growth medium, (Eagle's with Earle's salts (GIBCO BRL) containing 4.5 g/l glucose, 0.29 mg/ml L-glutamine, 1 mM sodium pyruvate, 15% heat-inactivated horse serum, antibiotics (penicillin-G 50 μg/ml, streptomycin 50 μg/ml, and neomycin 100 μg/ml) and 5 nM parathyroid hormone (PTH) 1–34 (Sigma)), and rocked gently (RedRocker™) at 37° C. in a 5% $CO_2$ humidified incubator for 17.5 hours preincubation. The concentration of PTH is chosen to insure maximum resorption.

Following preincubation, medium is removed and replaced with 1 ml/well of growth medium, as above, containing 20 or 30 μg/ml of the calcitonin mimetic in DMSO (final assay concentration of DMSO less than or equal to 1%). Positive controls which can be used include, growth medium containing 0.5, 1.0, 5.0 or 10 nM human calcitonin (hCT) and/or 0.01, 0.02, 0.05 or 0.2 nM salmon calcitonin (sCT). Control wells that do not receive PTH, human or salmon calcitonin or the calcitonin mimetic are included for determination of calcium release from untreated bones. All control wells contain a final assay concentration of DMSO equal to that present in the calcitonin mimetic treated wells.

Five bones are included in each sample group. Bones are incubated for 4, 8, 11, 24, 50.5, 72.5 and 98 hours. At each time point the media is removed and fresh dilutions of compound in media are added to the calvaria. After the media is removed, total calcium measurements are made using a Nova 7/7+7 Electrolyte Analyzed (Nova Biomedical) according to the manufacturer's specifications. Induction of bone resorption by PTH is seen as an increase in the concentration of calcium in the growth medium due to degradation of the bone matrix.

Human and salmon calcitonin and biologically active calcitonin mimetics inhibit the bone resorptive process as demonstrated by a lowering of the calcium in growth medium as compared to bones treated with PTH alone. The inhibitory effect of hCT and sCT is lost after a period of time, generally 24 hours, and the rate of resorption follows the same slope as that of PTH alone. Those mimetic compounds which do not have this escape will be able to continue inhibition of resorption for a longer period of time. Calvaria can also be observed, as described above, at each time point for signs of inhibition and signs of toxicity.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating a bone-related disorder, comprising administering to a subject suffering from such disorder an effective amount of a calcitonin mimetic of formula I:

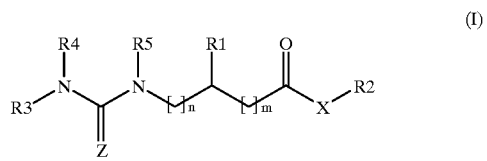

wherein

R1 and R2 are each members independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R3 is selected from the group consisting of hydrogen, aryl, substituted aryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R4 and R5 are each independently selected from the group consisting of hydrogen and alkyls having from 1 to 6 carbon atoms, or taken together from a ring selected from the group consisting of saturated or unsaturated five-member rings, saturated or unsaturated six-member rings and saturated or unsaturated seven-member rings;

Z and X are each independently selected from the group NH, O, S, or NR, wherein R is a lower alkyl group of from 1 to 6 carbon atoms; and n and m are each independently an integer from 0 to 6.

2. A method according to claim 1 wherein,

R1 is selected from the group consisting of phenyl, substituted phenyl, benzyl, substituted benzyl, naphthylmethyl, substituted naphthylmethyl, indolymethyl, and substituted indolymethyl;

R2 is selected from the group consisting of alkyls of from 1 to 6 carbon atoms, alkenyls of from 1 to 6 carbon atoms, benzyl, substituted benzyl, naphthylmethyl, and substituted naphthylmethyl;

wherein substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R4 and R5 are hydrogen;

Z is O; and

X is NH.

3. A method according to claim 2 wherein

R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl; and R2 is ethyl, allyl, benzyl or 2-naphthylmethyl.

4. A method according to claim 1, wherein said calcitonin mimetic has the formula:

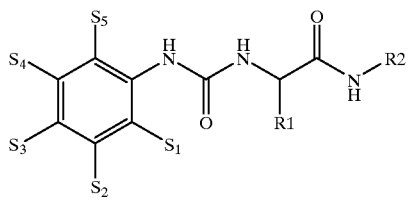

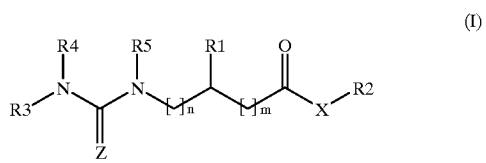

wherein,

R1 and R2 are each independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and S1, S2, S3, S4 and S5 are each independently selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

5. A method according to claim 1 wherein,

R1 is selected from the group consisting of phenyl, substituted phenyl, benzyl, substituted benzyl, naphthylmethyl, substituted naphthylmethyl, indolymethyl, and substituted indolymethyl;

R2 is selected from the group consisting of alkyls of from 1 to 6 carbon atoms, alkenyls of from 1 to 6 carbon atoms, benzyl, substituted benzyl, naphthylmethyl, and substituted naphthylmethyl;

wherein the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and S2 and S5 are t-butyl.

6. A method according to claim 5 wherein,

R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl;

R2 is ethyl, allyl, benzyl or 2-naphthylmethyl; and

S2 and S5 are t-butyl.

7. A method according to claim 1, wherein the bone-related disorder is selected from the group consisting of osteoporosis, Paget's disease, hyperparathyroidism, osteomalacia, periodontal applications (bone loss), hypercalcemia of malignancy and hypercalcemia of infancy.

8. A method of inhibiting bone resorption comprising administering to a subject in need of such inhibition an effective amount of a calcitonin mimetic of formula I:

wherein

R1 and R2 are each members independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R3 is selected from the group consisting of hydrogen, aryl, substituted aryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R4 and R5 are each independently selected from the group consisting of hydrogen and alkyls having from 1 to 6 carbon atoms, or taken together from a ring selected from the group consisting of saturated or unsaturated five-member rings, saturated or unsaturated six-member rings and saturated or unsaturated seven-member rings;

Z and X are each independently selected from the group NH, O, S, or NR, wherein R is a lower alkyl group of from 1 to 6 carbon atoms; and n and m are each independently an integer from 0 to 6.

9. A method according to claim 8 wherein,

R1 is selected from the group consisting of phenyl, substituted phenyl, benzyl, substituted benzyl, naphthylmethyl, substituted naphthylmethyl, indolymethyl, and substituted indolymethyl;

R2 is selected from the group consisting of alkyls having from 1 to 6 carbon atoms, alkenyls having from 1 to 6 carbon atoms, benzyl, substituted benzyl, naphthylmethyl, and substituted naphthylmethyl;

wherein substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

R4 and R5 are hydrogen;

Z is O; and

X is NH.

10. A method according to claim 8 wherein

R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl; and R2 is ethyl, allyl, benzyl or 2-naphthylmethyl.

11. A method according to claim 8, wherein said calcitonin mimetic has the formula:

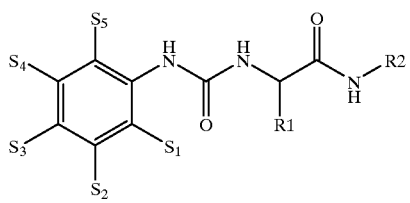

R1 and R2 are each independently selected from the group consisting of hydrogen, alkyls having from 1 to 6 carbon atoms, alkenyls having from 1 to 6 carbon atoms, aryl, substituted aryl, alkylaryl, substituted alkylaryl, carbocyclic ring, substituted carbocyclic ring, heterocyclic ring, substituted heterocyclic ring, and combinations thereof, the combinations are fused or covalently linked and the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and S1, S2, S3, S4 and S5 are each independently selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

12. A method according to claim 11 wherein,

R1 is selected from the group consisting of phenyl, substituted phenyl, benzyl, substituted benzyl, naphthylmethyl, substituted naphthylmethyl, indolymethyl, and substituted indolymethyl;

R2 is selected from the group consisting of alkyls having from 1 to 6 carbon atoms, alkenyls of from 1 to 6 carbon atoms, benzyl, substituted benzyl, naphthylmethyl, and substituted naphthylmethyl;

wherein the substituents are selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; and S2 and S5 are t-butyl.

13. A method according to claim 12 wherein,

R1 is 4-ethoxybenzyl, 1-ethyl-indolylmethyl, benzyl, 4-alloxybenzyl, 1-allyl-indolylmethyl, 4-chlorobenzyl, 4-flurobenzyl, 4-iodobenzyl, 2-naphthylmethyl or phenyl;

R2 is ethyl, allyl, benzyl or 2-naphthylmethyl; and

S2 and S5 are t-butyl.

* * * * *